US008950261B2

(12) United States Patent
Carradori et al.

(10) Patent No.: US 8,950,261 B2
(45) Date of Patent: Feb. 10, 2015

(54) FAULT DETECTION METHOD AND SYSTEM

(75) Inventors: Massimo Carradori, Napoli (IT); Paolo Rami, Napoli (IT); Gian Luca Pioppi, Napoli (IT)

(73) Assignee: Ansaldobreda S.p.A. (IT)

( * ) Notice: Subject to any disclaimer, the term of this patent is extended or adjusted under 35 U.S.C. 154(b) by 553 days.

(21) Appl. No.: 13/381,588

(22) PCT Filed: Jul. 2, 2010

(86) PCT No.: PCT/EP2010/059498
§ 371 (c)(1),
(2), (4) Date: May 1, 2012

(87) PCT Pub. No.: WO2011/000956
PCT Pub. Date: Jan. 6, 2011

(65) Prior Publication Data
US 2012/0208470 A1     Aug. 16, 2012

(30) Foreign Application Priority Data

Jul. 2, 2009  (EP) .................................. 09425258

(51) Int. Cl.
*G01N 29/11*     (2006.01)
*G01N 29/48*     (2006.01)
(Continued)

(52) U.S. Cl.
CPC ................. *G01N 29/11* (2013.01); *G01M 3/24* (2013.01); *G01N 29/265* (2013.01); *G01N 29/4427* (2013.01); *G01N 29/48* (2013.01); *G01N 2291/048* (2013.01); *G01N 2291/102* (2013.01)
USPC ................................. 73/592; 73/599; 73/602

(58) Field of Classification Search
USPC .............................. 73/592, 599, 602; 340/605
See application file for complete search history.

(56) References Cited

U.S. PATENT DOCUMENTS 3,768,306 A * 10/1973 Stearns ........................... 73/625
5,780,723 A     7/1998 Koo
(Continued)

FOREIGN PATENT DOCUMENTS

| DE | 4237527 A1 | 5/1994 |
| GB | 2388191 A | 11/2003 |
| JP | 2000304660 A | 11/2000 |

OTHER PUBLICATIONS

"International Application Serial No. PCT/EP2010/059498, International Search Report mailed Sep. 16, 2010", 4 pgs.
(Continued)

*Primary Examiner* — J M Saint Surin
(74) *Attorney, Agent, or Firm* — Schwegman Lundberg & Woessner, P.A.

(57) ABSTRACT

A method of detecting faults in a member having a first and second face opposite each other and communicating fluidically in the presence of at least one fault; the method including the steps of: generating a first sound signal by means of a transmitter, so that the first sound signal interacts with at least one portion of the first face of the member; arranging a receiver, configured to receive a second sound signal, close to a respective portion of the second face of the member corresponding to the portion of the first face, the second sound signal being the outcome of the first sound signal interacting with the member; moving the receiver, close to the second face of the member; generating a detection signal, by means of the receiver, as a function of the received second sound signal; calculating, at a number of instants $(t_1\text{-}t_N)$ in which the receiver is moved, respective detection values $(A\tau, B\tau, N\tau)$ of a quantity associated with the energy of the detection signal; and, in the event of at least one fault in the member, locating the fault on the basis of the detection values and of the positions assumed by the receiver at respective instants.

14 Claims, 8 Drawing Sheets

(51) Int. Cl.
  *G01M 3/24* (2006.01)
  *G01N 29/265* (2006.01)
  *G01N 29/44* (2006.01)

(56) References Cited

U.S. PATENT DOCUMENTS

| 5,804,731 | A | * | 9/1998 | Jaeggi | 73/636 |
| 7,194,908 | B2 | * | 3/2007 | Nenno et al. | 73/618 |
| 8,175,820 | B2 | * | 5/2012 | Hatanaka et al. | 702/39 |
| 8,559,696 | B2 | * | 10/2013 | Yamanaka et al. | 382/141 |
| 2007/0109138 | A1 | | 5/2007 | Farrell | |
| 2013/0000407 | A1 | * | 1/2013 | Fei et al. | 73/588 |

OTHER PUBLICATIONS

"International Application Serial No. PCT/EP2010/059498, Written Opinion mailed Sep. 16, 2010", 3 pgs.

* cited by examiner

FAULT DETECTION METHOD AND SYSTEM

PRIORITY CLAIM AND RELATED APPLICATIONS

This application is a nationalization under 35 U.S.C. 371 of PCT/EP2010/059498, filed Jul. 2, 2010 and published as WO 2011/000956 A1 on Jan. 6, 2011, which claims priority to European Patent Application Serial No. 09425258.2, filed on Jul. 2, 2009; which applications and publication are incorporated herein by reference in their entirety.

TECHNICAL FIELD

The present invention relates to a fault detection method and system, in particular for analysing water- and airtight sealing of vehicles or vehicle parts.

BACKGROUND ART

Currently used systems and methods for testing water— and airtight sealing of vehicles or vehicle parts—in particular, water—and airtight sealing of doors, windows or other vehicle parts involving sealing, seals, or other types of connections—comprise subjecting the test vehicle to simulated rain and/or storms. That is, at the end of the manufacturing stage, the vehicle is subjected to prolonged, powerful water jets, after which an operator visually inspects the inside of the vehicle for water. If the test proves positive, this means the watertightness of the part of the vehicle letting in water needs improving. Locating the fault, however, may prove difficult or even impossible, on account of the poor accuracy of the known method described. Very often, in fact, failure to accurately locate the fault makes it preferable to change the whole seal or reseal.

SUMMARY

Various examples provide a fault detection method and system designed to overcome the drawbacks of the prior art.

According to various examples, there are provided a fault detection method and system, such as are claimed in claims 1 and 8 respectively.

BRIEF DESCRIPTION OF THE DRAWINGS

A non-limiting embodiment will be described by way of example with reference to the accompanying drawings, in which.

DETAILED DESCRIPTION

Figure 1:
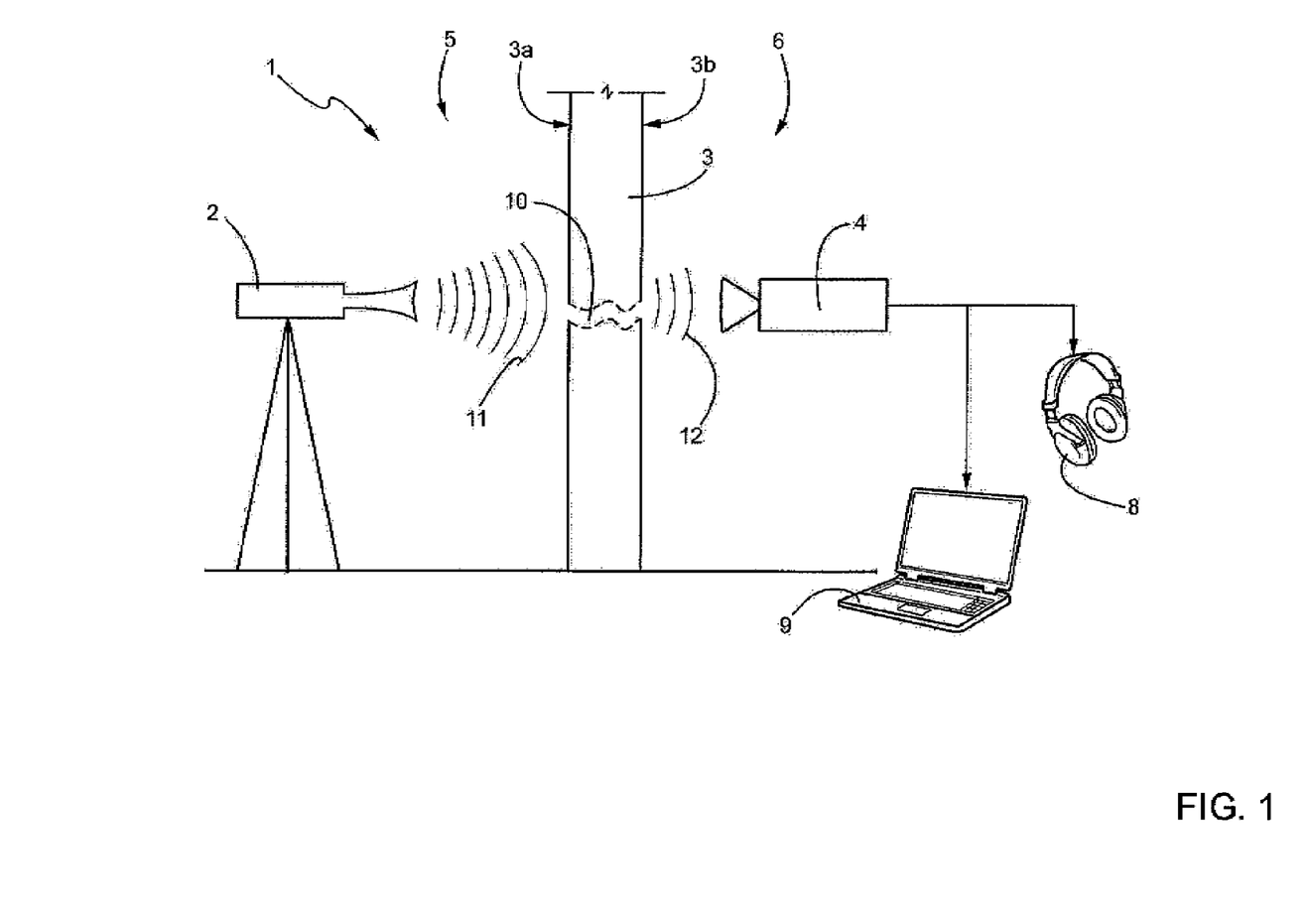
FIG. 1 shows a schematic of the system according to the present subject matter.

FIG. 1 shows a fault detection system 1 which employs a sound signal—in an inaudible frequency range, e.g. ultrasound—to analyze water—and airtight sealing of an insulating member 3, e.g. a bus or train door, a car window, etc.

Fault detection system 1 comprises an emitting device 2 located in a first environment 5, facing a first side 3a of insulating member 3, and configured to generate a sound signal, e.g. a 40 kHz±15 kHz frequency ultrasound signal; a receiving device 4 located in a second environment 6, facing a second side 3b of insulating member 3, and configured to receive the sound signal from emitting device 2 and convert it to an audible-frequency sound signal, e.g. ranging between 300 Hz and 2 kHz; a headset 8 connected to an output of receiving device 4 to enable an operator (not shown) to listen to the audible sound signal from receiving device 4; and a computer 9 connected to the output of receiving device 4 to process the audible sound signal and assist in identifying the fault (as described in detail below).

Emitting device 2 and receiving device 4 are advantageously an emitter and receiver of a known marketed ultrasound detector, e.g. a Soundscan 101 distributed by Sonatest Ltd.

In use, emitting device 2 may be fixed at a distance from first side 3a of insulating member 3 for testing, so that the sound signal, emitted with a given span α, covers a large enough test area of first side 3a.

As shown schematically in FIG. 1, insulating member 3 may comprise a fault 10, represented as a local fracture or opening in insulating member 3, extending the full thickness of insulating member 3 and connecting first environment 5 to second environment 6. In the event of such a fault 10, an incident sound wave 11, generated by emitting device 2 and travelling through first environment 5 onto side 3a, travels through fault 10 in insulating member 3 to produce a transmitted wave 12 travelling away from side 3b in second environment 6. Depending on the thickness and characteristics of insulating member 3, a transmitted wave may obviously travel between first and second environments 5 and 6, even in the absence of fault 10. Transmitted waves with and without fault 10, however, possess different energy, and can be distinguished accordingly, as explained in detail below.

In one embodiment, receiving device 4, in use, is moved manually by an operator (not shown) over second side 3b of insulating member 3 to scan the whole, or only critical portions (e.g. seals), of second side 3b of insulating member 3 and so pick up any transmitted waves 12 indicating a fault 10 in insulating member 3.

In an alternative embodiment, receiving device 4 may be moved automatically (not shown), e.g. on a robot arm and/or rails, etc., to safely scan portions of insulating member 3 not within easy reach of the operator.

Regardless of how receiving device 4 is moved, the operator can listen to the audible sound signal from receiving device 4 using headset 8 and, on the basis of the signal, immediately determine the presence of a fault 10 in the portion of insulating member 3 being scanned, and take immediate steps to accurately locate fault 10.

The audible sound signal from receiving device 4 is also sent to computer 9.

The audible sound signal may vary in both intensity and tone, depending on the energy of transmitted wave 12. Which means the operator can determine the presence of a fault 10 on the basis of both an increase in intensity and a variation in tone of the sound in headset 8. As explained in detail below, the audible sound signal from receiving device 4 comprises a number of audible frequencies characterizing the tone to be identified by the operator and associated with the presence or absence of a fault 10. The variation in intensity and tone depends on the frequencies of transmitted wave 12 and the energy associated with each frequency.

Figure 2:
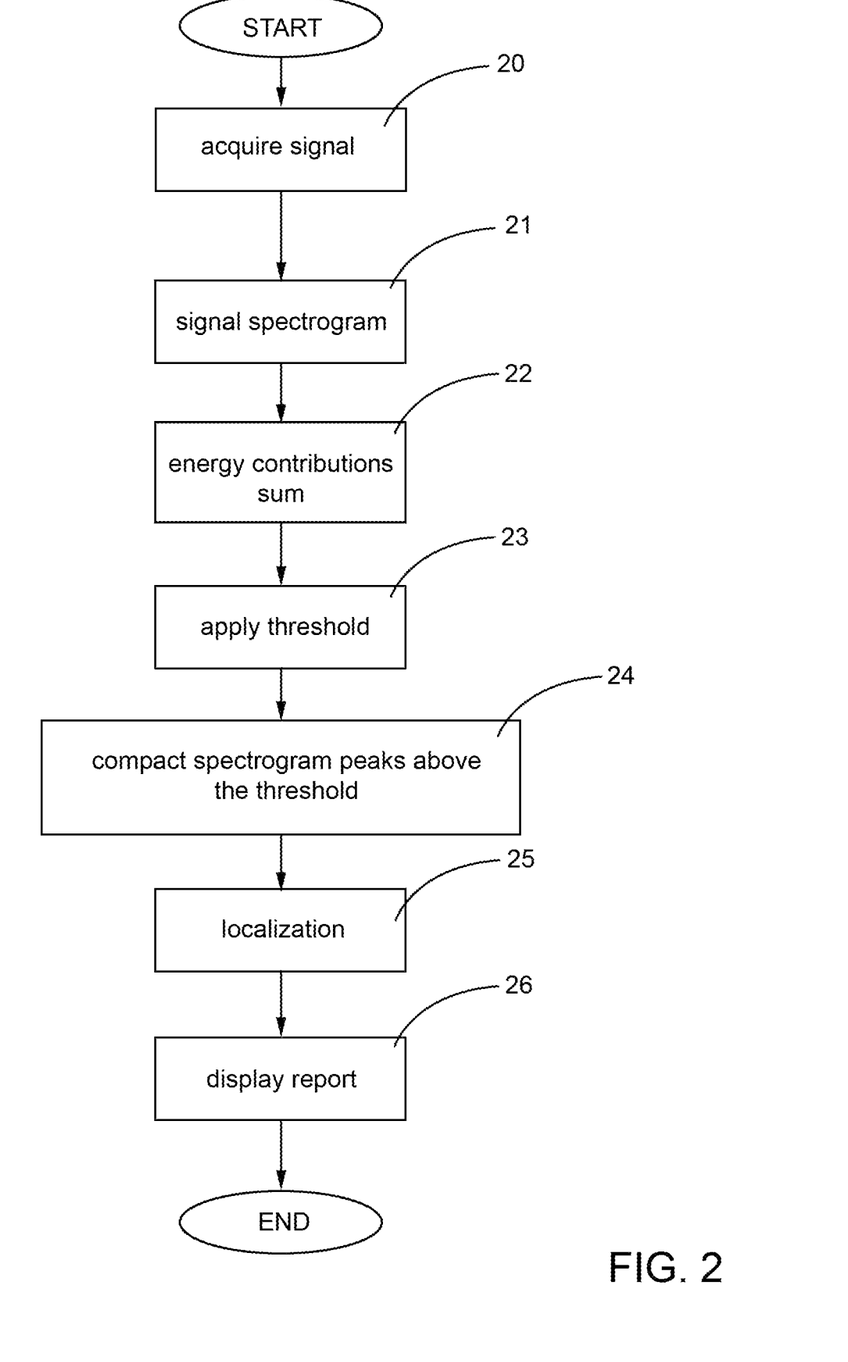
FIG. 2 shows a flow chart of the steps in the method according to the present subject matter.

FIG. 2 shows a flow chart of a fault detection method, that may be implemented, for example, as a software program in computer 9, in accordance with the present subject matter.

First (Step 20), the audible sound signal from receiving device 4 is acquired by computer 9 and sampled (e.g. at Nyquist rate) for conversion to a digitized audio signal, e.g. in "WAVEform" (also known simply as WAVE or WAV) audio format, though any other audio format, such as a compressed AAC or MP3 format, may be used.

Next (Step 21), the digitized audio signal is processed, in particular is Fourier (e.g. fast Fourier, FFT) transformed. More specifically, successive portions of the digitized audio signal are constant-band frequency analysed by FFT to produce, as is known, an energy spectrum.

FFT transformation of the digitized audio signal is conducted in successive time windows, e.g. each of 10 ms. Time windows of more or less than 10 ms may, of course, be used, though it is important to bear in mind that too short a time window would aggravate aliasing, thus altering the spectral estimate, whereas too long a time window could result in loss of useful information in identifying possible faults 10.

For example, a 30 s digitized audio signal and an FFT in successive 10 ms time windows give 3000 transform functions, each relating to a respective time window and associated with an instant in the window.

The time window may be of various types, e.g. rectangular, Hanning, Hamming or Barlett windows, or other known documented types.

The FFT can be performed in real time, calculating and displaying the energy spectrum of the transform function in less than or the same time as the length of the analysed signal, or at a later time.

Figure 3:
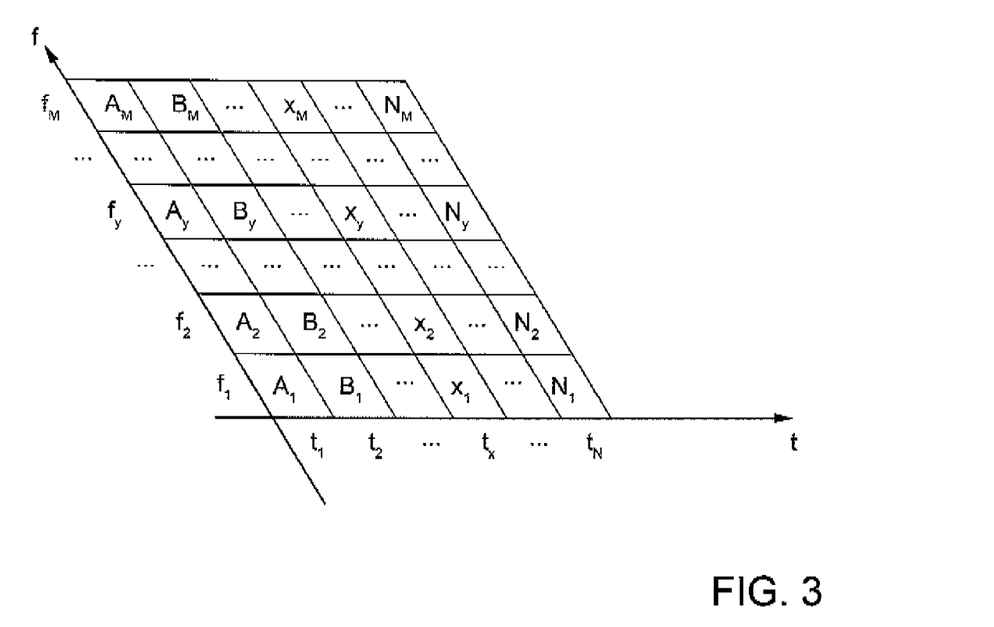
FIG. 3 shows a graph of a matrix during processing in accordance with the FIG. 2 flow chart method.

Changes over time in the digitized audio signal spectrum can be memorized in a matrix, e.g. of the type shown graphically in FIG. 3, having N number of columns $t_1, t_2, \ldots, t_X, \ldots, t_N$ (each relative to a respective instant) equal to the number of time windows used to cover the length of the digitized audio signal (3000 in the example referred to above), and M number of lines $f_1, f_2, \ldots, f_Y, \ldots, f_N$ (each relative to a frequency in the digitized signal spectrum) equal to the sound signal sampling frequency (e.g. M number of lines equal to the Nyquist rate).

The matrix so formed contains amplitude samples (e.g. expressed in dB) for each frequency $f_1$-$f_M$ at each instant $t_1$-$t_N$ considered. For example, as shown in the graph, the $t_1$ instant column contains samples $A_1$-$A_M$ for respective frequencies $f_1$-$f_M$; the $t_2$ instant column contains samples $B_1$-$B_M$ for respective frequencies $f_1$-$f_M$; the $t_X$ instant column contains samples $X_1$-$X_M$ for respective frequencies $f_1$-$f_M$; and so on.

Taking a Y-th row (indicating a Y-th frequency $f_Y$) in the matrix so formed, and working along the columns, it is possible to analyse the change over time in the Y-th frequency $f_Y$; similarly, given an X-th column (relative to an X-th instant) in the matrix, and working along the rows, it is possible to analyse the variation in amplitude of the digitized audio signal spectrum samples for different frequencies at that instant.

Figure 4:
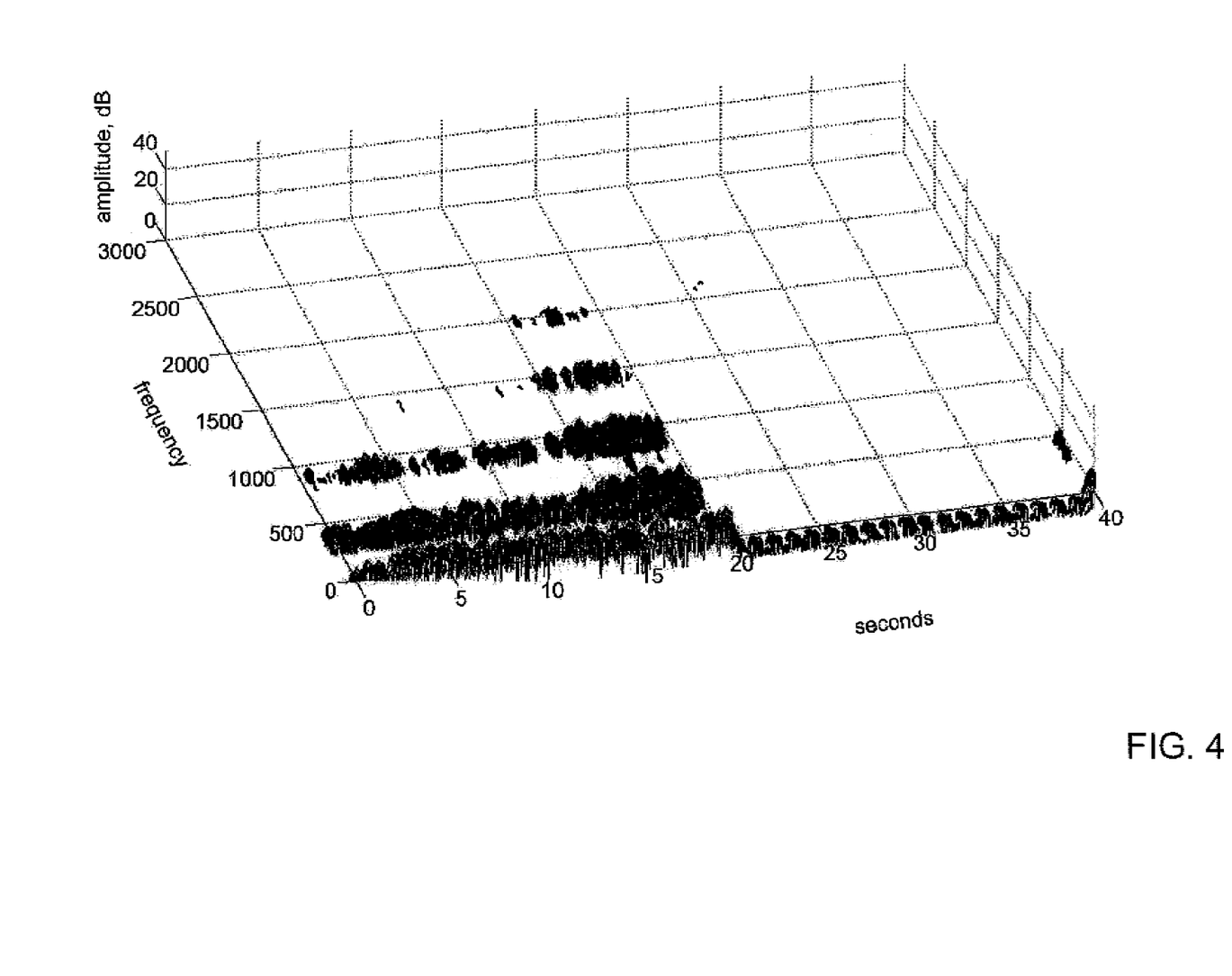
FIG. 4 shows a spectrogram of a sound signal during processing in accordance with the FIG. 2 flow chart method.

The matrix may also be represented graphically in the form of a waterfall diagram, sonogram or spectrogram, e.g. of the type shown in FIG. 4.

The frequencies of interest for the purpose of leakage and fault detection may be limited to specific frequencies, depending on the receiving device 4 employed. That is, receiving device 4 receives a transmitted sound wave 12 at a specific frequency, in particular the frequency of the ultrasound signal emitted by emitting device 2 (e.g. 40 kHz±15 kHz as stated). But converting the ultrasound signal to an audible sound signal produces an audible sound signal with its own characteristic frequency components, which obviously differ from those of the emitted ultrasound signal, and which depend on the desired tone of the sound signal. Amplitude depends on the desired intensity of the sound signal. For example, a low energy level of transmitted wave 12 may be associated with a low, weak tone, and a high energy level of transmitted wave 12 may be associated with a high, strong tone. Using a Sonatest Ltd Soundscan 101 as receiving device 4, the Applicant has found the significant frequency components of the audible sound signal to be located around 500 Hz, 1000 Hz for a low tone, and around 1500 Hz, 2000 Hz and 2500 Hz for a high tone. In the FIG. 3 example, substantial energy contributions can be observed around the 500 Hz and 100 Hz frequencies between 0 s and 20 s, and further contributions around the 1500 Hz and 2000 Hz frequencies, mainly between 15 s and 20 s. Zero Hz contributions represent the continuous component, which is not normally significant in determining the spectral estimate and, for the purposes of the method according to the present subject matter invention, can be ignored.

As can be seen, the most significant contributions, for all the frequencies, disregarding the continuous component, are between 15 s and 20 s.

A different receiving device 4 may obviously generate a sound signal with different significant frequency components. The significant frequencies of a generic receiving device 4 can be determined as follows.

An insulating member 3 with at least one fault 10, created if necessary for test purposes, is set up between emitting device 2 and receiving device 4. A sound signal is transmitted and received to pick up one or more transmitted waves 12 indicating fault 10 in insulating member 3. The audible sound signal from receiving device 4 is sent to computer 9 which converts it to a digitized audio signal. The digitized audio signal is processed as described in Step 21 in FIG. 2, i.e. undergoes a Fourier (e.g. fast Fourier, FFT) transform; and a 3D spectrogram or waterfall diagram (as shown, for example, in FIG. 4) is displayed, for example, on the screen of computer 9, so the operator can immediately determine, by eye or with the aid of the computer, the significant frequencies at fault 10 in the test insulating member 3.

Figure 5:
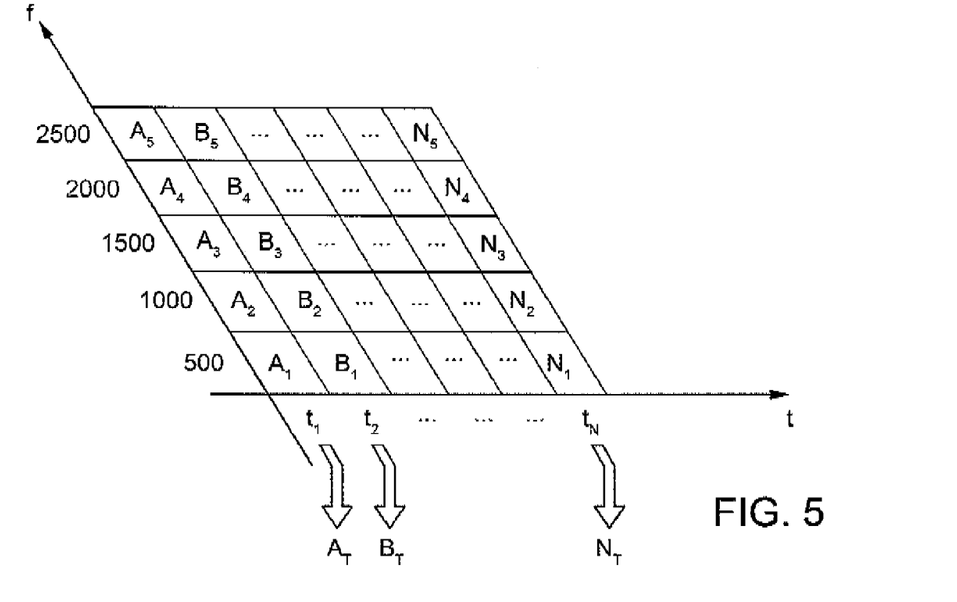
FIG. 5 shows a graph of a matrix during one example of possible processing in accordance with the FIG. 2 flow chart method.
Figure 6:
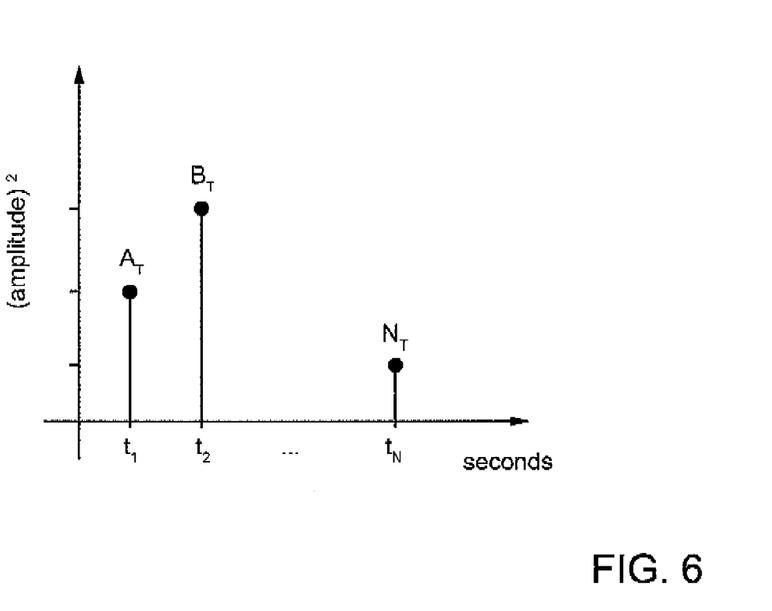
FIG. 6 shows a time graph of the variation in sound signal energy in the FIG. 5 example.

With reference to Step 22 in FIG. 2 and to FIGS. 5 and 6, for each instant $t_1$-$t_N$, the squares of the digitized signal spectrum amplitude samples of all the frequencies of interest (in the example shown, 500 Hz, 1000 Hz, 1500 Hz, 2000 Hz, 2500 Hz) are added to obtain respective energy contributions.

As shown in FIG. 5, in which only the frequencies of interest are shown for the sake of simplicity, a respective sample $A_1, A_2, A_3, A_4, A_5$ is present for each frequency at instant $t_1$; similarly, a respective sample $B_1, B_2, B_3, B_4, B_5$ is present for each frequency at instant $t_2$; and a respective sample $N_1, N_2, N_3, N_4, N_5$ is present for each frequency at the N-th instant $t_N$.

The squares of the respective samples at each instant $t_1$-$t_N$ are then added. For example, samples $A_1^2, A_2^2, A_3^2, A_4^2, A_5^2$ at instant $t_1$ are added to obtain energy contribution $A_T = A_1^2 +$ $A_2^2+A_3^2+A_4^2+A_5^2$; samples $B_1^2$, $B_2^2$, $B_2^2$, $B_3^2$, $B_4^2$, $B_5^2$ at instant $t_2$ are added to obtain energy contribution $B_T = B_1^2 + B_2^2 + B_3^2 + B_4^2 + B_5^2$; and so on.

This gives the FIG. 6 graph, in which each instant $t_1, t_2, \ldots, t_N$ is associated with a respective sum $A_T, B_T, \ldots, N_T$.

The FIG. 7 graph is obtained from the FIG. 4 spectrogram as described with reference to FIGS. 5 and 6. As can be seen, in this case, the energy contributions are smaller at the instants between 0 s and 15 s, and are higher between 15 s and 20 s. To determine which energy contributions are significant in identifying faults 10, a contribution amplitude discrimination threshold is set.

More specifically—Step 23 in FIG. 2—the discrimination threshold is defined using a variation of Rabiner's algorithm, which is known in literature, for example, from L. R. Rabiner, M. R. Sambur "An algorithm for determining the endpoints of isolated utterances", Bell Syst. Tech. J 1975.

First of all, on the basis of the FIG. 4 energy contributions obtained as described above, the maximum energy contribution IMX (peak value) and the minimum energy contribution IMN (silent condition energy value) are considered, and a first and second energy value i1 and i2 are calculated according to the following equations (1) and (2) respectively:

$$i1 = 0.03 \cdot (IMX - IMN) + IMN \quad (1)$$

$$i2 = 4 \cdot IMN \quad (2)$$

Equation (1) calculates a peak energy percentage (in this case, 3%), and equation (2) a value equal to 4 times the minimum energy contribution IMN. Though Rabiner's algorithm calculates the first and second energy value i1 and i2 according to equations (1) and (2), the 3% percentage in equation (1) and/or the 4 value in equation (2) may obviously vary if testing or practice show any advantage is to be gained.

A value ITM=max(i1, i2), equal to the maximum value of first and second energy values i1, i2, is then taken.

The ITM value is then multiplied by a compensation value COMP to obtain a value ITU=ITM·COMP. An ideal COMP value according to Rabiner's algorithm is 5, though other compensation values may be used. Substantially, compensation values below 5 lower the discrimination threshold value, and compensation values of over 5 increase the discrimination threshold value.

Finally, the value of a discrimination threshold 40 is obtained by taking half of the value ITU=ITM·COMP.

In a variation of the algorithm described, after calculating first and second energy values i1 and i2 according to equations (1) and (2), a value ITL=min(i1, i2), equal to the minimum value of first and second energy values i1 and i2, is taken, and is multiplied by compensation value COMP—again equal, for example, to 5—to obtain a value ITL=ITM·COMP, which is used as discrimination threshold 40.

In general terms, the discrimination threshold adaptively varies between a peak value (IMX) and a noise value (IMN) of the detection values, as a function of the peak value and of the noise value. The peak value may be regarded as the highest value among said detection values and the noise value may be regarded as the lowest value among said detection values.

Figure 7:
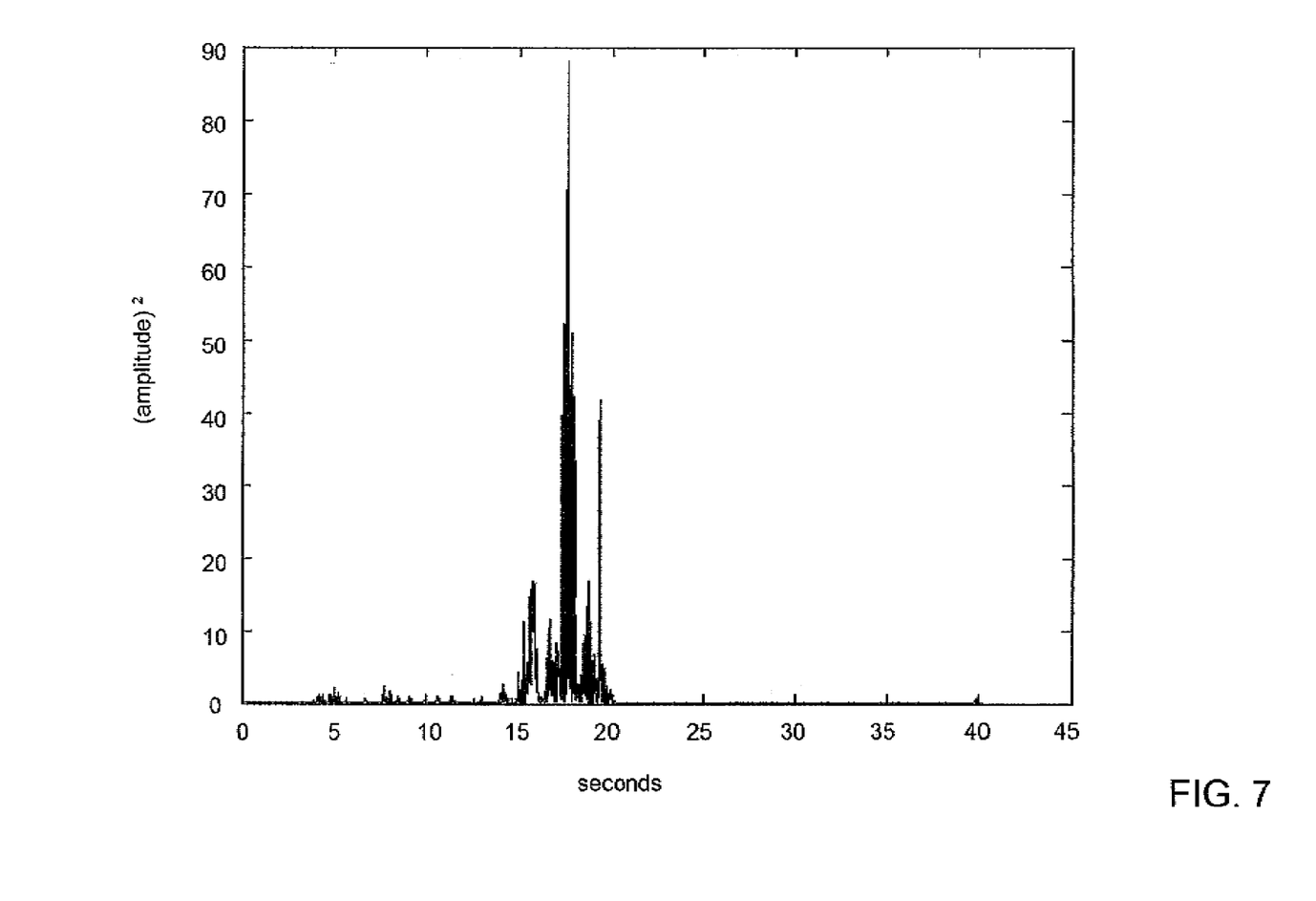
FIG. 7 shows a time graph of the variation in energy of the sound signal shown in the FIG. 4 spectrogram.
Figure 8:
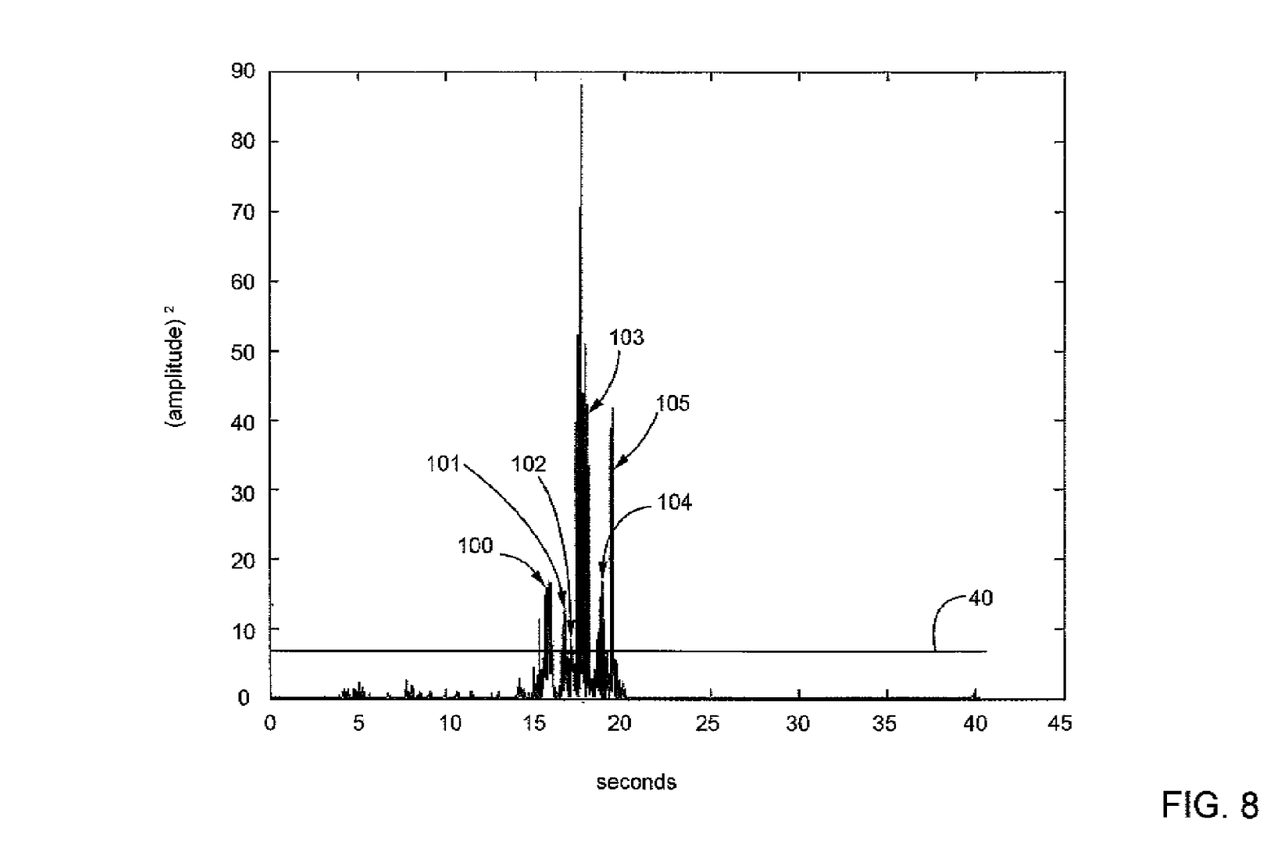
FIG. 8 shows a time graph of the variation in energy of the FIG. 7 sound signal with a superimposed discrimination threshold.

FIG. 8 shows the FIG. 7 spectrogram with a superimposed discrimination threshold 40 calculated as described using Rabiner's algorithm (the discrimination threshold 40 is thus an adaptive threshold). Energy contributions below discrimination threshold 40 are rejected, and energy contributions above discrimination threshold 40 are taken to indicate a fault 10.

At this stage, the actual location of any faults 10 in insulating member 3 is still unknown, but the time interval in which the faults are detected is known.

With reference to FIG. 2, Step 24, to locate faults 10 in insulating member 3, the FIG. 8 spectrogram energy contributions above discrimination threshold 40 are compacted to group together any closely consecutive energy contributions that as a whole exceed discrimination threshold 40 for at least 1 second.

This choice substantially depends on the required degree of precision in locating faults 10. More specifically, working on the basis of the known space=speed·time equation, a given scanning speed of insulating member 3 by receiving device 4 (e.g. 0.2 m/s) and a given desired spatial location precision (e.g. grouping together faults 10 within a 20 cm space range of insulating member 3) give a 1 s time range in which to discriminate between faults 10.

Obviously, by altering scanning speed or the discrimination time range, the degree of precision in spatially locating a fault 10 can be altered as required.

Given the shape of the analysed portion of insulating member 3, mean scanning speed, and the scanning path, fault 10 can be spatially located in the analysed portion of insulating member 3 by determining the time interval in which fault 10 is detected.

Figure 9:
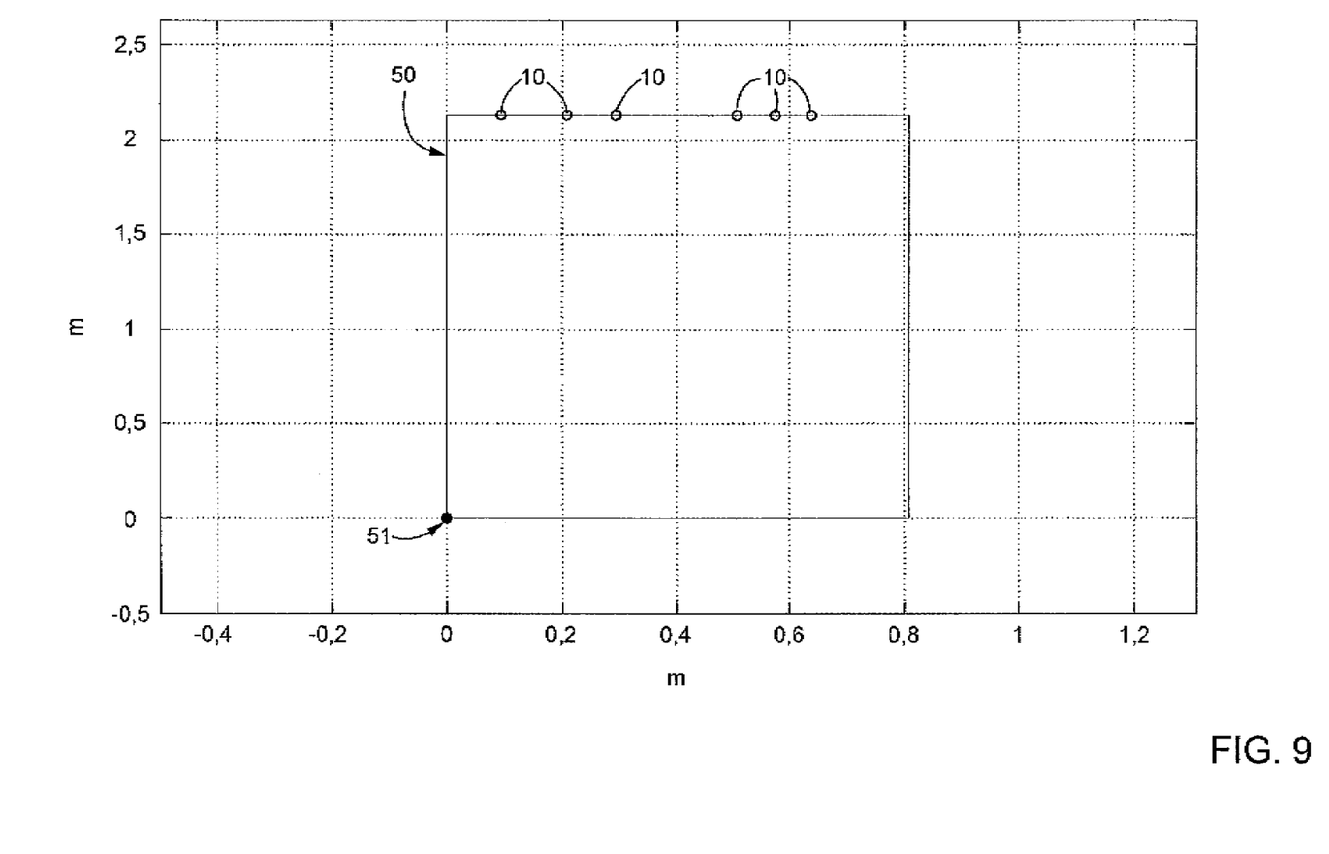
FIG. 9 shows a computerized schematic of a rectangular element with defects detected using the method according to the present subject matter invention.

FIG. 9 shows a schematic of the perimeter of a rectangular insulating member 3, of which a peripheral portion 50 has been analysed in search of faults 10. The drawing shows six faults 10 along the perimeter of insulating member 3, corresponding to respective energy contributions in FIG. 8 which exceed discrimination threshold 40 for at least 1 second, are indicated 100-105 in FIG. 8, and are located between 15 and 20 seconds.

Obviously, to match the spatial location and detection time of a fault 10, the scanning start point and path must be known. In the example shown, scanning starts at the bottom left-hand corner 51 of insulating member 3, and proceeds clockwise along peripheral portion 50 of insulating member 3 back to the start point at corner 51.

The Applicant has conducted numerous tests to determine the reliability of the method according to the present subject matter. In particular, data has been collected relative to: true positives (VP), i.e. correctly detected faults 10; true negatives (VN), i.e. correctly identified areas with no faults 10; false positives (FP), i.e. faults 10 wrongly detected by the method according to the present subject matter; and false negatives (FN), i.e. undetected faults 10. Values relative to the following parameters were calculated on the basis of the above data sensitivity, calculated as (VP)/(VP+FN), which represents the ability of the method according to the present subject matter to detect faults 10; specificity, calculated as (VN)/(VN+FP), which represents the ability of the method according to the present subject matter to determine areas with no defects 10; positive prediction value, calculated as (VP)/(VP+FP), which represents the probability of correctly detecting a fault 10; and negative prediction value, calculated as (VN)/(VN+FN), which represents the probability of correctly detecting no fault 10.

According to the Applicant's findings, the best sensitivity, specificity, and positive and negative prediction values are achieved with emitting device 2 positioned facing the barycentre of insulating member 3 (or, at any rate, substantially centred with respect to insulating member 3). As regards the distance of emitting device 2 from insulating member 3, the Applicant has conducted numerous tests at different distances, and in particular with the emitting device contacting the insulating member (0 cm), at a distance ranging between 25 cm and 50 cm, and at a distance of over 50 cm. Tests show the best results, with reference to the above parameters, are achieved positioning emitting device 2 at a distance of 25-50 cm from insulating member 3.

In the above optimum conditions, the Applicant has recorded, on average, sensitivity values of over 0.75, specificity values of over 0.9, a positive prediction value of over 0.8, and a negative prediction value of over 0.9.

The embodiments described for the calculation of the adaptive threshold 40 disclose a method (in particular, based on the Rabiner's algorithm) for computing a threshold value which is a function of a maximum energy contribution IMX (peak value) and a minimum energy contribution IMN (silent condition energy value). The IMX and IMN values may vary (and, typically, they do) during each measuring operation, depending on a plurality of environmental conditions (such as noise, materials being inspected, etc.). The threshold 40 adaptively varies between the two values IMN and IMX since it autonomously changes its own value to adapt itself to changes in the environmental conditions during inspection operation (such a changes are reflected by a variation of IMX and/or IMN values).

The advantages of the fault detection method and system according to the present subject matter will be clear from the above description.

For example, in the event receiving device 4 is moved automatically, e.g. by a robot arm and/or on rails, the fault detection method may be fully automated and so not require full-time operator assistance.

Moreover, computer 9 processing of the signal received by receiving device 4, as in the method described, minimizes the possibility of error in identifying faults 10, as compared with known technology, which depends on subjective interpretation of the sound received simply in a headset by the test operator.

Furthermore, the fault detection system can be transported easily, in view of the light weight of emitting device 2, receiving device 4, and computer 9.

Finally, the fact that the discrimination threshold is an adaptive threshold, brings the advantage that a specific threshold for each specific vehicle or compartment being analyzed can be adaptively set at the end of the inspection process, without the need for storing one or a plurality of predefined threshold values. This means that a plurality of vehicles compartments may be inspected without the need for providing a specific threshold for each vehicle compartment. Moreover, the inspection results are minimally dependent from environmental conditions, possibly present during the inspection, which interfere with the inspection process and may affect the results. In fact, in the case that all the acquired signals are deviated by a certain quantity, also the calculated threshold is deviated by a corresponding quantity. As a consequence, the inspection results are accurate even in the presence of disturbances.

Clearly, changes may be made to the fault detection method and system according to the present subject matter without, however, departing from the scope of the present subject matter as defined in the accompanying claims.

For example, in addition to detecting faults in vehicles or vehicle parts, the method and system described may also be used for analysing sealings and seals, e.g. of pipes or conduits. In which case, emitting device 2 is positioned facing the inlet of the pipe or conduit, so the emitted signal travels along the inside of the pipe or conduit; and one or more receiving devices 4 are located at the monitored seals or sealings, and are moved to analyse the whole seal or sealing in search of faults.

Though FIG. 1 shows a headset 8 connected to the output of receiving device 4, headset 8 is obviously not essential, in that testing can be carried out by the method as described in FIG. 2 and implemented in computer 9, regardless of the presence of an operator.

Moreover, the system may be automated using servo-mechanisms for automatically moving receiving device 4 and emitting device 2.

Moreover, data need not necessarily be processed as soon as it is acquired. That is to say, all the data may be acquired and recorded on a storage medium for subsequent remote processing. Alternatively, acquired data may be transmitted over Internet to a remote computer, so processing can be carried out at any distance from the data acquisition location.

The invention claimed is:

1. A method of detecting faults in a member, said member having a first and second face opposite each other and communicating fluidically in the presence of at least one fault; the method comprising the steps of:

generating a first sound signal with a transmitter, so that said first sound signal interacts with at least one portion of the first face of the member;

arranging a receiver, configured to receive a second sound signal, close to a respective portion of said second face of the member corresponding to said portion of said first face, said second sound signal being the outcome of said first sound signal interacting with said member;

moving said receiver, close to the second face of the member;

generating a detection signal with the receiver, as a function of the received said second sound signal;

calculating, at a number of instants ($t_i \sim t_N$) in which said receiver is moved, respective detection values ($A_\tau$, $B_\tau$, $N_\tau$) of a quantity associated with the energy of said detection signal; and in the event of said at least one fault in said member:

locating the fault on the basis of said detection values and of the positions assumed by said receiver at the respective instants, calculating a discrimination threshold, adaptively varying between a peak value (IMX) and a noise value (IMN) of said detection values as a function of said peak value and noise value the peak value being the highest value among said detection values and the noise value being the lowest value among said detection values, and acquiring a spectrogram of said detection signal for a number of frequencies ($f_i \sim f_M$) and said number of instants ($t_i \sim t_N$), so as to associate a respective amplitude value ($A_i$-$A_M$; $B_i$-$B_M$, $X_i$-$X_M$; $N_i$-$N_M$) with each pair defined by a frequency in said number of frequencies, and an instant in said number of instants; and, for each of the instants in said number of instants, summing the amplitude values associated with the same instant, to obtain said detection values ($A_\tau$, $B_T$, $N_T$) of said quantity associated with the energy of said detection signal.

2. The method as claimed in claim 1, wherein said first sound signal is an inaudible-frequency signal, and said step of generating a detection signal comprises the step of converting the received said second sound signal to an audible-frequency signal.

3. The method as claimed in claim 1, wherein said locating step comprises:

determining the presence of said at least one fault when at least one of said detection values ($A_\tau$, $B_T$, $N_T$) exceeds said discrimination threshold; determining the position assumed by said receiver at the instant associated with said at least one of said detection values; and determining the location of said at least one fault as a function of said position assumed by said receiver.

4. The method as claimed in claim 3, wherein said step of determining the presence of said at least one fault comprises determining said presence when a predetermined number of consecutive detection values among said detection values exceed said discrimination threshold.

5. The method as claimed in claim 3, wherein the step of defining a discrimination threshold comprises the steps of:
acquiring the peak value (IMX);
acquiring the noise value (IMN);
calculating a percentage value of said peak value (IMX);
multiplying said noise value (IMN) by a proportionality factor;
acquiring the maximum value (ITU) of said peak value and said noise value;
multiplying said maximum value (ITU) of said peak value and said noise value by a compensation factor; and calculating a fraction of said maximum value (ITU).

6. The method as claimed in claim 3, wherein the step of defining a discrimination threshold comprises the steps of:
acquiring the peak value (IMX);
acquiring the noise value (IMN);
calculating a percentage value of said peak value (IMX);
multiplying said noise value (IMN) by a proportionality factor;
acquiring the minimum value (ITL) of said peak value and said noise value; and
multiplying said minimum value (ITL) of said peak value and said noise value by a compensation factor.

7. A system for detecting faults in a member, said member having a first and a second face opposite each other and communicating fluidically in the presence of at least one fault; said system comprising:
a transmitter positioned facing a portion of the first face of the member, and configured to generate an inaudible-frequency sound signal;
a receiver positioned movably facing a portion of the second face of the member, and configured to receive the sound signal generated by the transmitter and convert it to an audible-frequency detection signal; and
processing means for:
receiving the detection signal;
calculating, at a number of instants ($t_1$-$t_N$) in which the receiver is moved, respective detection values ($A_\tau$, $B_\tau$, $N_\tau$) of a quantity associated with the energy of said detection signal;
in the event of said at least one fault in said member, locating the fault on the basis of said detection values and of the positions assumed by said receiver at respective instants;
calculating, as a function of a peak value (IMX) and a noise value (IMN) of said detection values, a discrimination threshold adaptively varying between the peak value and the noise value, the peak value being the highest value among said detection values and the noise value being the lowest value among said detection values; and
acquiring a spectrogram of said detection signal for a number of frequencies (fi-$f_M$) and said number of instants (ti~$t_N$), so as to associate a amplitude value (Ai-$A_M$; Bi-$B_M$, Xi-$X_M$; Ni-$N_M$) with each pair defined by a frequency in said number of frequencies and an instant in said number of instants; and, for all the instants in said number of instants, to sum the amplitude values associated with the same instant, to obtain said detection values ($A_\tau$, $B_\tau N_\tau$) of said quantity associated with the energy of said detection signal.

8. The system as claimed in claim 7, wherein said first sound signal is an inaudible-frequency signal, and said processing means are for converting the received said second sound signal to an audible-frequency signal.

9. The system as claimed in claim 7, wherein said processing means are for:
determining the presence of said at least one fault when at least one of said detection values ($A_\tau$, $B_T$, $N_T$) exceeds said discrimination threshold; determine the position assumed by said receiver at the instant associated with said at least one of said detection values; and
determining the location of said at least one fault as a function of said position assumed by said receiver.

10. The system as claimed in claim 9, wherein said processing means are for determining said presence of said at least one fault when a predetermined number of consecutive detection values among said detection values exceed said discrimination threshold.

11. The system as claimed in claim 9, wherein said processing means are for:
acquiring the peak value (IMX);
acquiring the noise value (IMN);
calculating a percentage value of said peak value (IMX);
multiplying said noise value (IMN) by a proportionality factor;
acquiring the maximum value (ITU) of said peak value and said noise value;
multiplying said maximum value (ITU) of said peak value and said noise value by a compensation factor; and calculating a fraction of said maximum value (ITU).

12. The system as claimed in claim 9, wherein said processing means are for:
acquiring the peak value (IMX);
acquiring the noise value (IMN);
calculating a percentage value of said peak value (IMX);
multiplying said noise value (IMN) by a proportionality factor;
acquiring the minimum value (ITL) of said peak value and said noise value; and
multiplying said minimum value (ITL) of said peak value and said noise value by a compensation factor.

13. A system for detecting faults in a member, said member having a first and a second face opposite each other and communicating fluidically in the presence of at least one fault; said system comprising:
a transmitter positioned facing a portion of the first face of the member, and configured for generating an inaudible-frequency sound signal;
a receiver positioned movably facing a portion of the second face of the member, and configured for receiving the sound signal generated by the transmitter and convert it to an audible-frequency detection signal; and
a processor configured to:
receive the detection signal;
calculate, at a number of instants ($t_1$-$t_N$) in which the receiver is moved, respective detection values ($A_\tau$, $B_\tau$, $N_\tau$) of a quantity associated with the energy of said detection signal;
in the event of said at least one fault in said member, locate the fault on the basis of said detection values and of the positions assumed by said receiver at respective instants;
calculate, as a function of a peak value (IMX) and a noise value (IMN) of said detection values, a discrimination threshold adaptively varying between the peak value and the noise value the peak value being the highest value among said detection values and the noise value being the lowest value among said detection values; and acquire a spectrogram of said detection signal for a number of frequencies ($f_i$-$f_M$) and said number of instants ($t_i$~$t_N$), so as to associate a amplitude value ($A_i$-$A_M$; $B_i$-$B_M$, $X_i$~$X_M$; $N_i$~$N_M$) with each pair defined by a frequency in said number of frequencies and an instant in said number of instants; and, for all the instants in said number of instants, to sum the amplitude values associated with the same instant, to obtain said detection values ($A_\tau$, $B_\tau N_\tau$) of said quantity associated with the energy of said detection signal.

14. The system as claimed in claim 13, wherein said first sound signal is an inaudible-frequency signal, and said processor is configured to convert the received said second sound signal to an audible-frequency signal.

\* \* \* \* \*